(12) United States Patent
Denton et al.

(10) Patent No.: US 9,541,540 B2
(45) Date of Patent: Jan. 10, 2017

(54) NON-DESTRUCTIVE TEST INSPECTION METHOD FOR EVALUATING THERMAL DEGRADATION OF BISMALEIMIDE RESIN

(71) Applicant: United Technologies Corporation, Hartford, CT (US)

(72) Inventors: Jeffrey Denton, Jackson, MI (US); James H. Stewart, Holt, MI (US); William Bogue, Hebron, CT (US)

(73) Assignee: United Technologies Corporation, Farmington, CT (US)

( * ) Notice: Subject to any disclaimer, the term of this patent is extended or adjusted under 35 U.S.C. 154(b) by 578 days.

(21) Appl. No.: 14/046,652

(22) Filed: Oct. 4, 2013

(65) Prior Publication Data

US 2014/0096350 A1 Apr. 10, 2014

Related U.S. Application Data

(60) Provisional application No. 61/709,801, filed on Oct. 4, 2012.

(51) Int. Cl.
*G01N 33/44* (2006.01)
*G01N 21/25* (2006.01)
*G01N 21/3563* (2014.01)

(52) U.S. Cl.
CPC .............. *G01N 33/44* (2013.01); *G01N 21/25* (2013.01); *G01N 21/3563* (2013.01); *Y10T 29/49769* (2015.01)

(58) Field of Classification Search
CPC .... G01N 21/3563; G01N 33/44; G01N 21/25; Y10T 29/49769

USPC ......................................... 29/407.04; 702/33
See application file for complete search history.

(56) References Cited

U.S. PATENT DOCUMENTS

| | | | |
|---|---|---|---|
| 7,115,869 B2 | 10/2006 | Shelly et al. | |
| 7,510,372 B2 | 3/2009 | Bogue et al. | |
| 7,572,347 B2 | 8/2009 | Bogue | |
| 7,614,848 B2 | 11/2009 | Bogue et al. | |
| 7,622,178 B2 | 11/2009 | Bogue et al. | |
| 7,645,479 B2 | 1/2010 | Bogue et al. | |
| 7,650,678 B2 | 1/2010 | Bogue | |
| 7,665,963 B2 | 2/2010 | Bogue et al. | |
| 7,695,585 B2 | 4/2010 | Bogue et al. | |
| 7,727,349 B2 | 6/2010 | Holland et al. | |
| 2005/0067569 A1* | 3/2005 | Shelley | G01N 21/55 250/341.8 |
| 2007/0019917 A1* | 1/2007 | Bayindir | C03B 37/026 385/123 |

(Continued)

OTHER PUBLICATIONS

Donnellan et al., "Relationships in a Bismaleimide Resin System. Part I: Cure Mechanisms", Polmyer Engineering and Science, vol. 32, No. 6, Mar. 1992, pp. 409-414.

*Primary Examiner* — Lisa Caputo
*Assistant Examiner* — Philip Cotey
(74) *Attorney, Agent, or Firm* — O'Shea Getz P.C.

(57) ABSTRACT

A non-destructive method for determining an amount of temperature exposure to a Bismaleimide Resin (BMI) matrix substrate, the method includes determining component data of a Bismaleimide Resin (BMI) matrix component via fourier transform infrared (FTIR) spectroscopy; correlating the component data to model data to determine a structural debit from temperature exposure; and bounding a structurally damaged area in response to the correlating.

15 Claims, 8 Drawing Sheets

(56) References Cited

U.S. PATENT DOCUMENTS

| | | | | |
|---|---|---|---|---|
| 2008/0134883 A1* | 6/2008 | Kumar | ................ | B01D 53/228 95/45 |
| 2009/0323757 A1* | 12/2009 | Werner | ................ | G01N 25/72 374/45 |
| 2010/0038544 A1* | 2/2010 | Shelley | .............. | G01N 21/3563 250/339.09 |
| 2010/0140476 A1* | 6/2010 | Werner | .................... | G01J 3/02 250/339.07 |
| 2010/0276578 A1* | 11/2010 | Shelley | .............. | G01N 21/3563 250/252.1 |
| 2011/0001047 A1* | 1/2011 | Shelley | .............. | G01N 21/3563 250/341.8 |
| 2011/0108731 A1* | 5/2011 | Shelley | ................ | G01N 21/274 250/341.8 |

* cited by examiner

NON-DESTRUCTIVE TEST INSPECTION METHOD FOR EVALUATING THERMAL DEGRADATION OF BISMALEIMIDE RESIN

The present disclosure claims priority to U.S. Provisional Patent Disclosure Ser. No. 61/709,801, filed Oct. 4, 2012.

BACKGROUND

The present disclosure relates to an inspection method, and more particularly to a non-destructive test (NDT) method using Fourier-Transform Infra-Red (FT-IR) spectrometry.

Composite materials are utilized in a variety of applications. These composite materials may be exposed to thermal degradation in a variety of circumstances, ranging from fire to lightning strikes to weapons impacts.

Visual examination of the thermal degradation may be inadequate to properly bound damaged areas during aftermarket maintenance service. Visual examination methods may require relatively excessive removal of material beyond visual evidence of damage to ensure that degraded composite material is removed. This relatively excessive removal may increase the complexity of the repair.

SUMMARY

A non-destructive method for determining an amount of temperature exposure to a Bismaleimide Resin (BMI) matrix substrate, the method according to one disclosed non-limiting embodiment of the present disclosure includes determining component data of a Bismaleimide Resin (BMI) matrix component via fourier transform infrared (FTIR) spectroscopy; correlating the component data to model data to determine a structural debit from temperature exposure; and bounding a structurally damaged area in response to the correlating.

A further embodiment of the present disclosure includes deeming areas on the component serviceable/unserviceable with respect to the bounding.

A further embodiment of any of the foregoing embodiments of the present disclosure includes confirming component construction is of a Bismaleimide Resin (BMI) matrix.

A further embodiment of any of the foregoing embodiments of the present disclosure includes correlating the component data to model data within a molecular spectroscopy analyzer.

A further embodiment of any of the foregoing embodiments of the present disclosure includes initially locating the molecular spectroscopy analyzer within a visually indicated thermal stress area denoted by a discoloration on the substrate of the component.

A further embodiment of any of the foregoing embodiments of the present disclosure includes moving the molecular spectroscopy analyzer outward toward an edge of the visually indicated thermal stress area to bound a structurally damaged area.

A further embodiment of any of the foregoing embodiments of the present disclosure includes moving the molecular spectroscopy analyzer with respect to a grid pattern.

A further embodiment of any of the foregoing embodiments of the present disclosure includes determining the model data from a multiple of post conditioned test panels.

A further embodiment of any of the foregoing embodiments of the present disclosure includes performing short beam shear to relate strength characteristics to exposure temperature for each of the multiple of post conditioned test panels.

A further embodiment of any of the foregoing embodiments of the present disclosure includes determining failure criteria in response to the short beam shear and exposure temperature for each of the multiple of post conditioned test panels.

A further embodiment of any of the foregoing embodiments of the present disclosure includes correlating the model data to remaining strength.

A non-destructive method for determining an amount of temperature exposure to a Bismaleimide Resin (BMI) matrix substrate, the method according to another disclosed non-limiting embodiment of the present disclosure includes locating a molecular spectroscopy analyzer within a visually indicated thermal stress area denoted by a discoloration on a substrate of a component; and moving the molecular spectroscopy analyzer outward toward an edge of the visually indicated thermal stress area to bound a structurally damaged area.

A further embodiment of any of the foregoing embodiments of the present disclosure includes, wherein the structurally damaged area is within the discoloration.

A further embodiment of any of the foregoing embodiments of the present disclosure includes moving the molecular spectroscopy analyzer with respect to a grid pattern to bound a structurally damaged area.

A further embodiment of any of the foregoing embodiments of the present disclosure includes removing the structurally damaged area.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
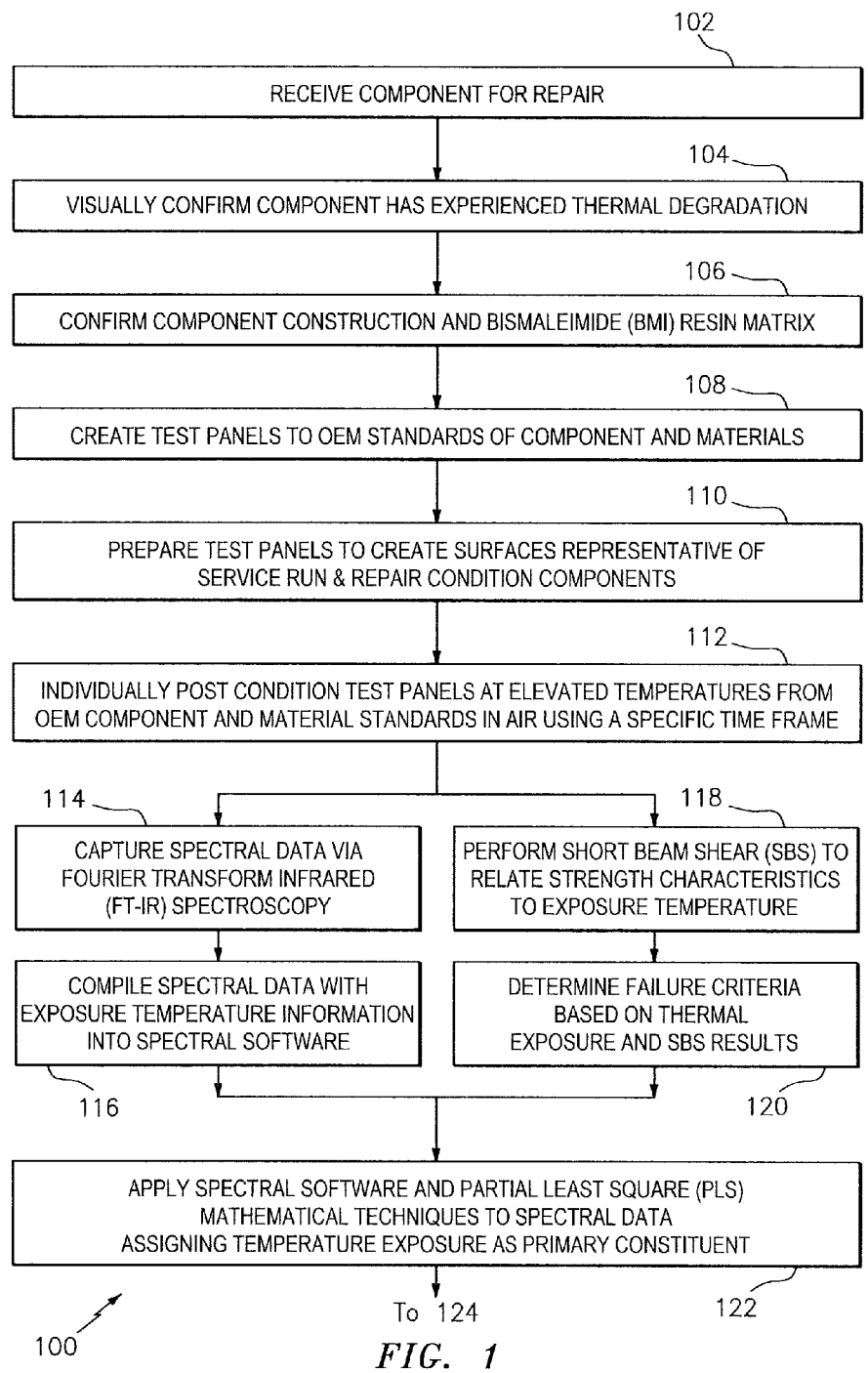
FIG. 1 is a flowchart of a non-destructive test (NDT) method according to one disclosed non-limiting embodiment.
Figure 1:
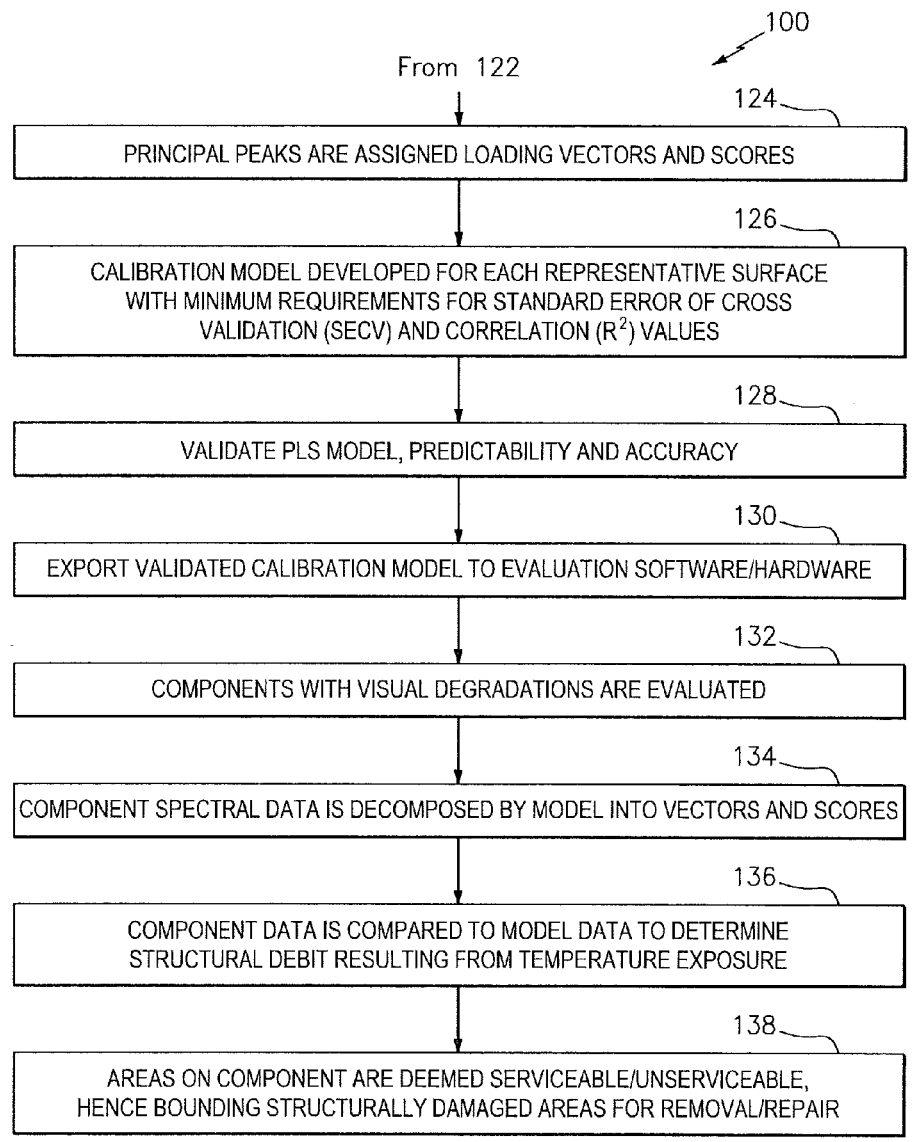
Figure 2:
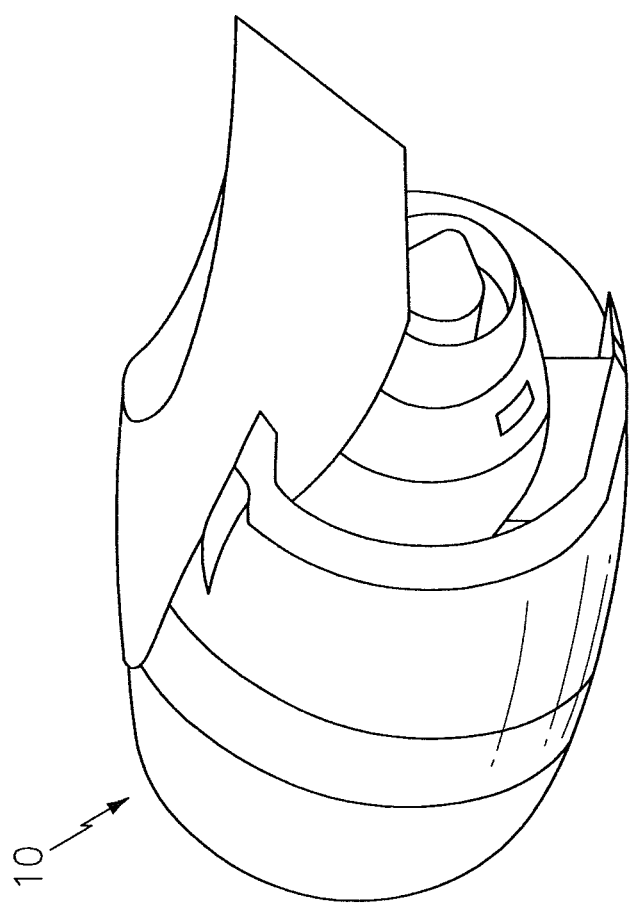
FIG. 2 is a schematic view of an example component which may be inspected with the method of FIG. 1.

FIG. 1 illustrates one disclosed non-limiting embodiment of a non-destructive test (NDT) method 100. The method 100 initially includes visual confirmation that a component 10 (FIG. 2) has experienced thermal degradation (step 102, 104) and is manufactured of a Bismaleimide (BMI) resin matrix (step 106) in a carbon fiber substrate. The component 10 in this example is a Bismaleimide (BMI) resin matrix carbon fiber substrate component of a gas turbine engine nacelle (FIG. 2), however, various BMI components will benefit herefrom.

Next, test panels manufactured to Original Equipment Manufacturer (OEM) standards of component and materials (step 108) equivalent to the component 10 are prepared to create surfaces representative of service run and repair condition components (step 110). That is, the test panels are representative of the component 10 with respect to, for example, resin matrix, substrate, service time and/or repaired conditions thereof.

Each of the test panels are then individually post conditioned with respect to a predefined range of conditions representative of thermal degradation (step 112). The predefined range of conditions, for example, may include different temperatures for different time periods to simulate the response of the component 10 to thermal degradation induced by, for example, fire, lightning, bleed valve air during flight, or other conditions.

Next, spectral data via fourier transform infrared (FTIR) spectroscopy for each of the test panels is determined (step 114) then compiled with the exposure temperature information of the range of conditions representative of thermal degradation (step 116). The test panels are also subjected to short beam shear (SBS) tests to relate strength characteristics to the range of conditions representative of thermal degradation (step 118). The thermal exposure and SBS results are then utilized to determine failure criteria (step 120).

Determination of the failure criteria may be performed in one disclosed non-limiting embodiment by, for example, spectral software and partial least square (PLS) mathematical techniques applied to the spectral data to correlate the spectral data with temperature exposure as the primary constituent (step 122). In one disclosed non-limiting embodiment, principle peaks are designated (step 124) to develop a calibration model for each representative post conditioned test panel with minimum requirements for, for example, standard error of cross validation (SECV) and correlation (R squared) values (step 126). That is, particular spectra peaks at particular wave numbers, and/or peak to peak ratios thereof but not limited to, may be utilized to correlate the spectral data with temperature exposure to determine model data representative of remaining strength of the substrate.

The model data is then validated with spectra of known exposure and strength values (step 128) and exported to a molecular spectroscopy analyzer (step 130) such as a 4100 ExoScan Series FTIR manufactured by Agilent Technologies of California, USA. It should be appreciated that various hand-held infrared filter spectrometer may be utilized. In alternative embodiments, an infrared Fourier transform imaging spectrometer, or a portable infrared spectrometer may be utilized.

Figure 3:
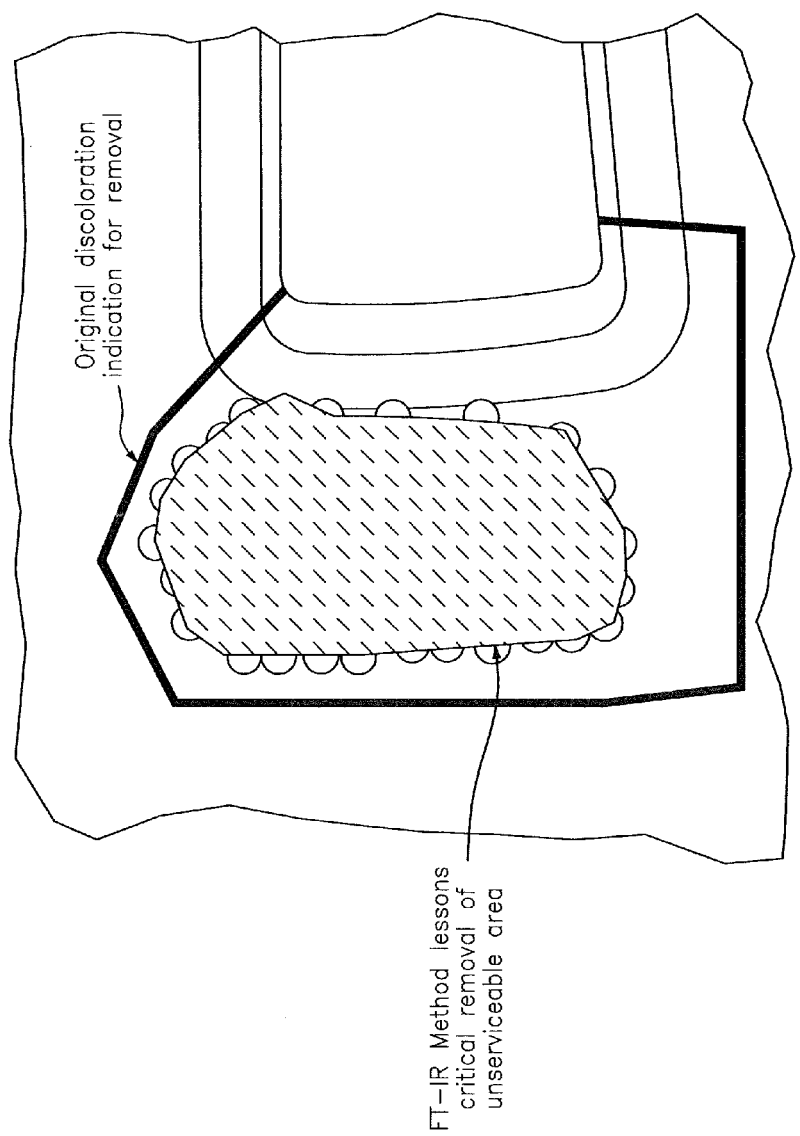
FIG. 3 is an expanded schematic view of an example substrate of the component of FIG. 2 which may be inspected with the method of FIG. 1.

The component 10 is then visually evaluated (step 132; FIG. 3). Typically, the outermost edge of visual thermal stress is typically denoted by discoloration. The discoloration itself, however, may not define the unserviceable area that must be replaced. That is, the unserviceable area is contained within the discoloration area but the entirety of the discoloration area may not be unserviceable. The entirety of the discoloration region has heretofore been removed to ensure that any degraded composite material is removed, however, this relatively excessive removal may increase the complexity and expense of the repair. Moreover, this method may also determine the discoloration area to be entirely serviceable according to OEM strength requirements for the laminate substrate.

The molecular spectroscopy analyzer decomposes component spectral data into vectors and scores the data (step 134) such that the component data is compared to model data to determine the structural debit resulting from temperature exposure (step 136). In one disclosed non-limiting embodiment, the molecular spectroscopy analyzer provides the user with a serviceable or unserviceable indication from temperature exposure. That is, the Molecular Spectroscopy analyzer trued by the calibration model quantifiably identifies the degraded area to minimize the repair extent and thereby reduce repair costs or negate entirely. Areas of degradation are correlated to remaining strength to allow structural acceptance or rejection of minor thermal damage.

Figure 4:
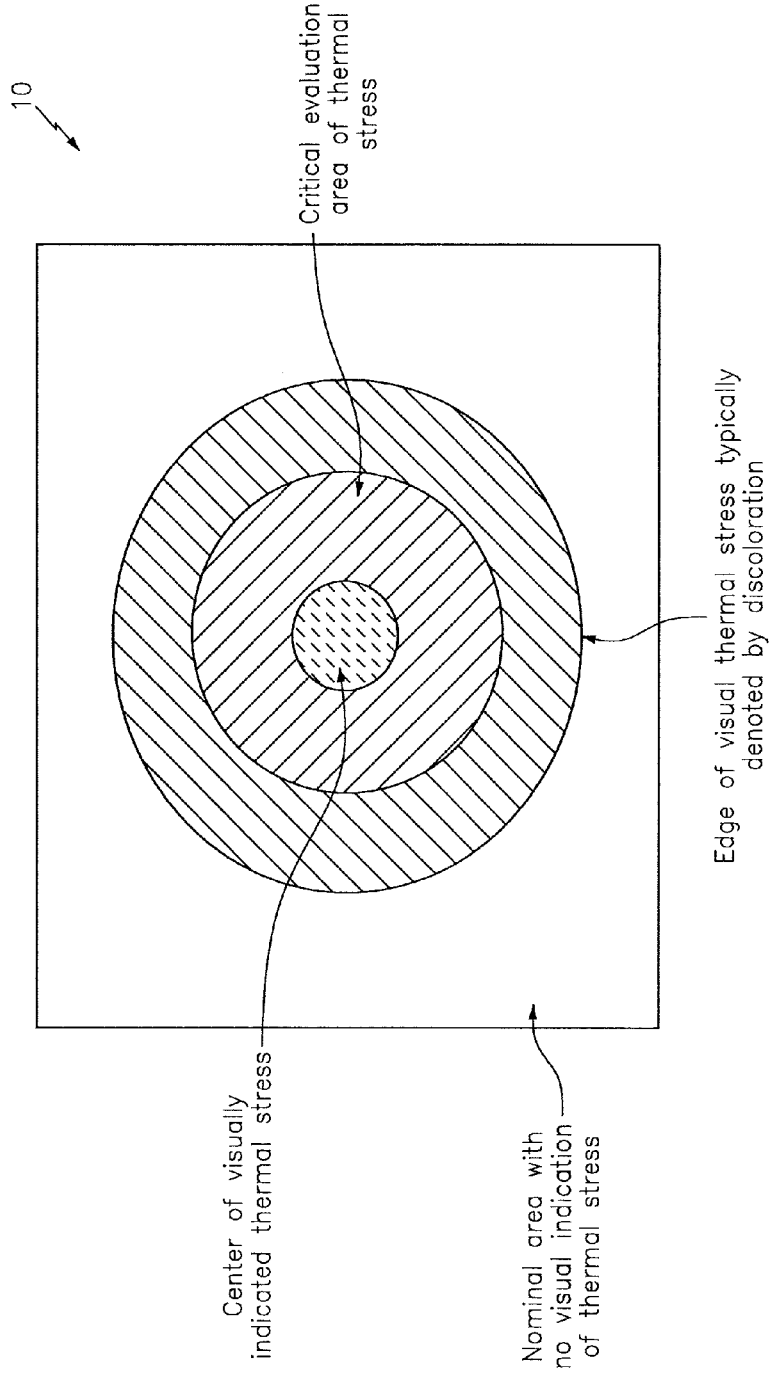
FIG. 4 is a schematic view of thermal damage to a substrate of the example workpiece.
Figure 5:
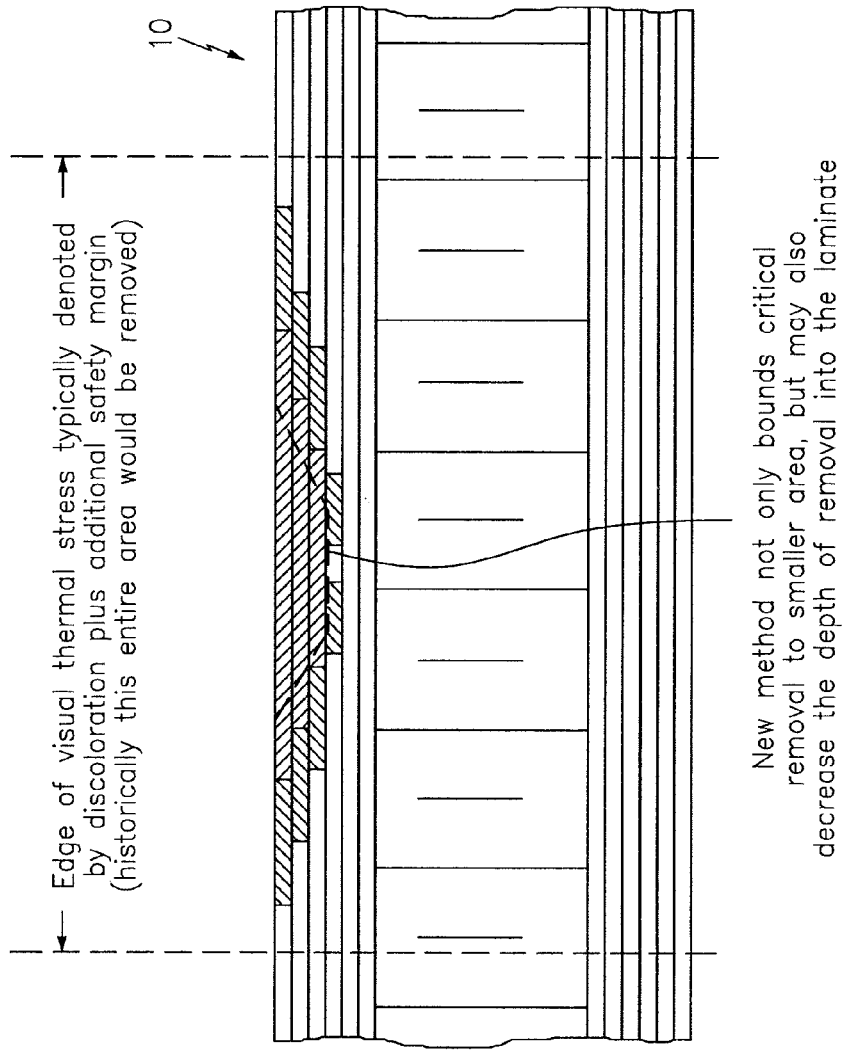
FIG. 5 is a sectional view of thermal damage to an example honeycomb workpiece.
Figure 6:
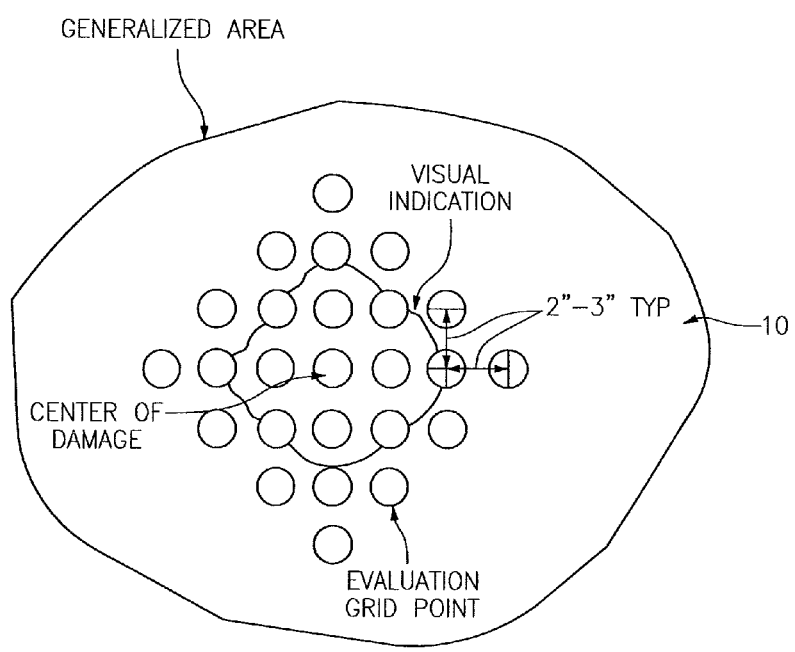
FIG. 6 is a schematic view of the movement of a molecular spectroscopy analyzer with respect to a grid pattern.

The molecular spectroscopy analyzer is then located generally at center of the visually indicated the mal stress area of the component 10 and moved outward toward the edge of the visual thermal stress denoted by the discoloration within a critical evaluation area of the thermal stress to deem areas on the component 10 either serviceable or unserviceable and thereby bound the structurally damaged areas for removal/repair (step 138; FIGS. 4 and 5). The molecular spectroscopy analyzer may be moved by a user in a grid pattern (FIG. 6) with, for example, two to three inches (50-75 mm) between measurement points. It should be appreciated that the locations may be moved closer together as the user approaches the critical evaluation area.

Figure 7:
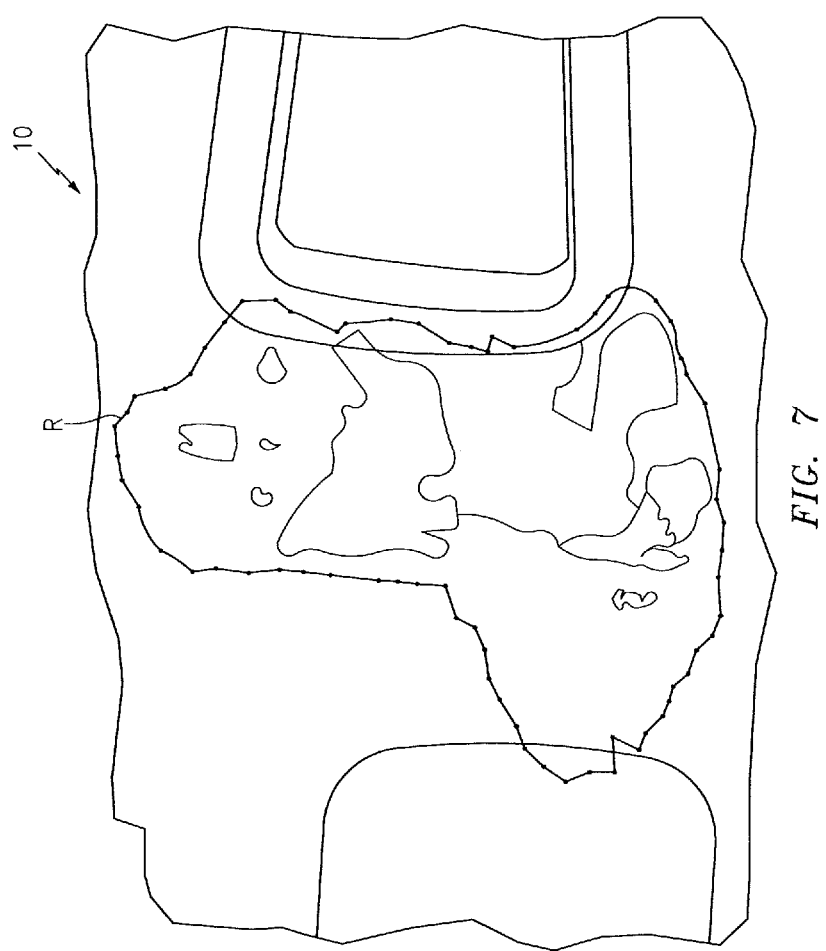
FIG. 7 is a schematic view of a structurally damaged area as bounded by the method of FIG. 1.

The NDT method specifically bounds the repair area 12 (FIG. 7) of BMI composite parts during aftermarket service maintenance and qualify laminates as serviceable that have areas of possible thermal exposure. The application of this method will produce a cost savings as the BMI composite component by not scrapping the part.

The use of the terms "a" and "an" and "the" and similar references in the context of description (especially in the context of the following claims) are to be construed to cover both the singular and the plural, unless otherwise indicated herein or specifically contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other. It should be appreciated that relative positional terms such as "forward," "aft," "upper," "lower," "above," "below," and the like are with reference to the normal operational attitude of the vehicle and should not be considered otherwise limiting.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason the appended claims should be studied to determine true scope and content.

What is claimed:

1. A non-destructive method for determining an amount of temperature exposure to a Bismaleimide Resin (BMI) matrix substrate, the method comprising:
   determining component data of a Bismaleimide Resin (BMI) matrix component via fourier transform infrared (FTIR) spectroscopy;
   correlating the component data to model data to determine a structural debit from temperature exposure; and
   bounding a structurally damaged area in response to the correlating.

2. The method as recited in claim 1, further comprising deeming areas on the component serviceable/unserviceable with respect to the bounding.

3. The method as recited in claim 1, further comprising confirming component construction is of a Bismaleimide Resin (BMI) matrix.

4. The method as recited in claim 1, further comprising correlating the component data to model data within a molecular spectroscopy analyzer.

5. The method as recited in claim 4, further comprising initially locating the molecular spectroscopy analyzer within a visually indicated thermal stress area denoted by a discoloration on the substrate of the component.

6. The method as recited in claim 5, further comprising moving the molecular spectroscopy analyzer outward toward an edge of the visually indicated thermal stress area to bound a structurally damaged area.

7. The method as recited in claim 6, further comprising moving the molecular spectroscopy analyzer with respect to a grid pattern.

8. The method as recited in claim 6, further comprising determining the model data from a multiple of post conditioned test panels.

9. The method as recited in claim 8, further comprising performing short beam shear to relate strength characteristics to exposure temperature for each of the multiple of post conditioned test panels.

10. The method as recited in claim 9, further comprising determining failure criteria in response to the short beam shear and exposure temperature for each of the multiple of post conditioned test panels.

11. The method as recited in claim 6, further comprising correlating the model data to remaining strength.

12. A non-destructive method for determining an amount of temperature exposure to a Bismaleimide Resin (BMI) matrix substrate, the method comprising:
    locating a molecular spectroscopy analyzer within a visually indicated thermal stress area denoted by a discoloration on a substrate of a component; and
    moving the molecular spectroscopy analyzer outward toward an edge of the visually indicated thermal stress area to bound a structurally damaged area.

13. The method as recited in claim 12, wherein the structurally damaged area is within the discoloration.

14. The method as recited in claim 12, further comprising moving the molecular spectroscopy analyzer with respect to a grid pattern to bound a structurally damaged area.

15. The method as recited in claim 12, further comprising removing the structurally damaged area.

* * * * *